US00PP17176P2

(12) United States Plant Patent
Talmadge

(10) Patent No.: US PP17,176 P2
(45) Date of Patent: Oct. 31, 2006

(54) ***DIASCIA* PLANT NAMED 'BALWINWITE'**

(50) Latin Name: *Diascia×hybrida*
Varietal Denomination: Balwinwite

(75) Inventor: Paul A. Talmadge, Orcutt, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/296,046

(22) Filed: Dec. 7, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Plant Breeders' Rights application No. 2005/1997 filed Oct. 25, 2005.

*Primary Examiner*—Kent Bell
*Assistant Examiner*—Annette H Para
(74) *Attorney, Agent, or Firm*—Audrey Charles

(57) ABSTRACT

A new and distinct cultivar of *Diascia* plant named 'Balwinwite' characterized by its white-colored flowers, medium green-colored foliage, and moderately vigorous, upright and spreading growth habit.

1 Drawing Sheet

Latin name of genus and species of plant claimed: *Diascia×hybrida.*
Variety denomination: 'Balwinwite'.

BACKGROUND OF THE INVENTION

The present invention relates to a new and distinct cultivar of *Diascia* plant botanically known as *Diascia×hybrida* and hereinafter referred to by the cultivar name 'Balwinwite'.

The new cultivar originated in a controlled breeding program in Guadalupe, Calif. during December 2002. The objective of the breeding program was the development of *Diascia* cultivars with a well-branched, upright and spreading growth habit, continuous flowering, and medium green-colored foliage.

The female (seed) parent of the new cultivar was the proprietary *Diascia×hybrida* breeding selection designated 2008-2-2-3-2, not patented, characterized by its large white-colored flowers, dark green-colored foliage, and upright growth habit. The male (pollen) parent of the new cultivar was the proprietary *Diascia×hybrida* breeding selection designated 3384-4-1-1, not patented, characterized by its blush white-colored flowers, medium green-colored foliage, and prostrate growth habit. The new *Diascia* was discovered and selected by the inventor as a single flowering plant within the progeny of the above stated cross-pollination during March 2003 in a controlled environment at Guadalupe, Calif.

Asexual reproduction of the new cultivar by terminal stem cuttings since March 2003 at Guadalupe, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balwinwite' as a new and distinct cultivar of *Diascia* plant:

1. White-colored flowers;
2. Medium green-colored foliage; and
3. Moderately vigorous, upright and spreading growth habit.

Plants of the new cultivar differ from plants of the female parent primarily in foliage color and growth habit and from plants of the male parent primarily in flower color and growth habit.

Of the many commercially available *Diascia* cultivars known to the inventor, the most similar in comparison to the new cultivar is 'Balwhiswhit', U.S. Plant Pat. No. 15,188. However, in side by side comparisons, plants of the new cultivar differ from plants of 'Balwhiswhit' in the following characteristics:

1. Plants of the new cultivar are shorter than plants of 'Balwhiswhit';
2. Plants of the new cultivar have darker green-colored foliage than plants of 'Balwhiswhit'; and
3. Plants of the new cultivar have a flower color different from plants of 'Balwhiswhit'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balwinwite'. The plants were grown in 10 cm pots for 7 weeks in a greenhouse at West Chicago, Ill.

DETAILED BOTANICAL DESCRIPTION

Figure 1:
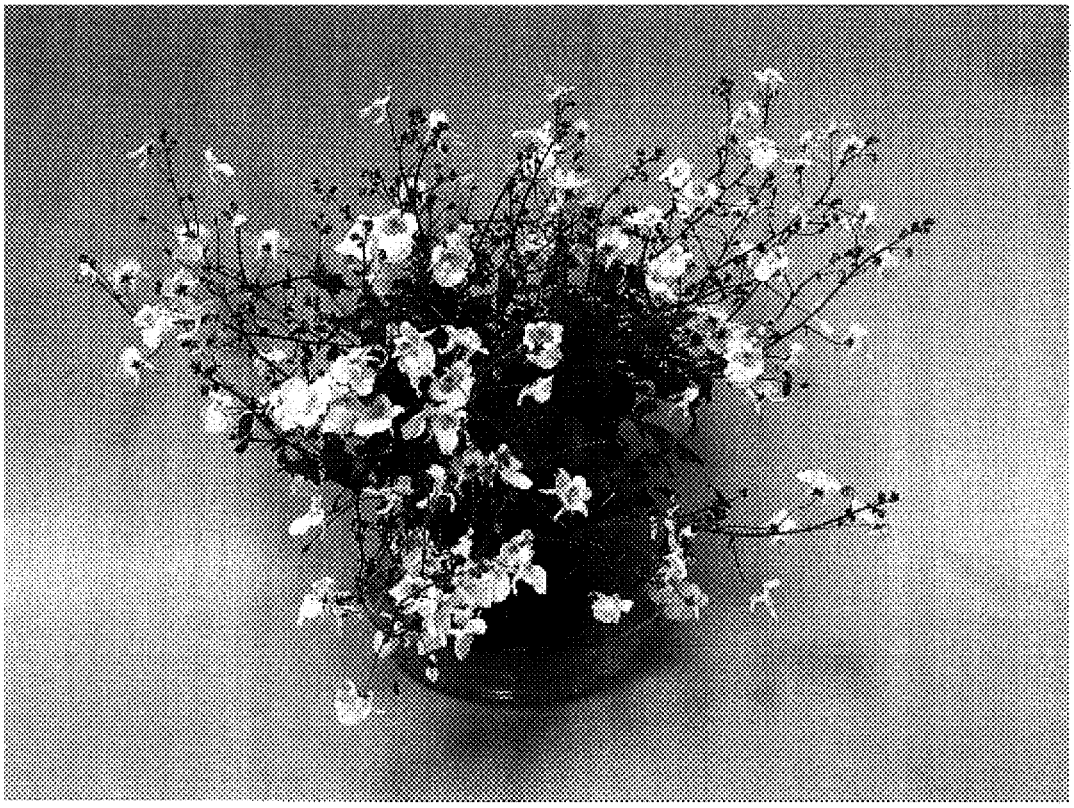
FIG. 1 illustrates a side view of the overall growth and flowering habit of 'Balwinwite'.
Figure 2:
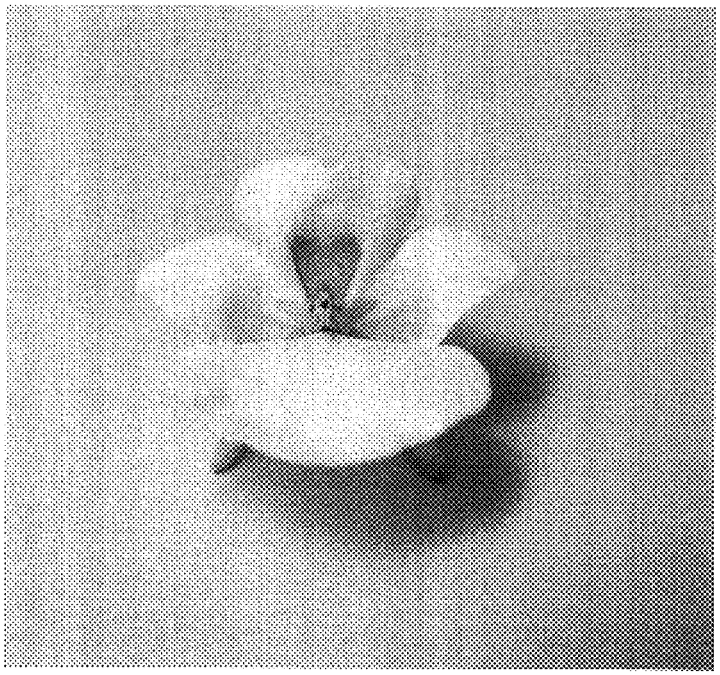
FIG. 2 illustrates a close-up view of an individual flower of 'Balwinwite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 11, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 7 weeks utilizing a soilless growth medium. Greenhouse temperatures were maintained at approximately 62° F. to 75° F. (17° C. to 24° C.) during the day and approximately 52° F. to 60° F. (11° C. to 15° C.) during the night. Greenhouse light levels of 5,000 to 8,000 footcandles were maintained during the day.

Botanical classification: *Diascia×hybrida* cultivar Balwinwite.

Parentage:

*Female parent.*—Proprietary *Diascia×hybrida* breeding selection designated 2008-2-2-3-2, not patented.

*Male parent.*—Proprietary *Diascia×hybrida* breeding selection designated 3384-4-1-1, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Crop time.*—Approximately 5 to 7 weeks from a rooted cutting.

*Growth habit and general appearance.*—Moderately vigorous, upright and spreading.

*Size.*—Height from soil level to top of plant plane: Approximately 16.8 cm. Width: Approximately 45.0 cm.

*Branching habit.*—Freely basal branching. Pinching improves branching. Approximately 8 branches per plant with lateral branches potentially forming at every node.

*Branch.*—Strength: Moderate. Shape: Square in cross section. Length: Approximately 26.2 cm. Diameter: Approximately 1.5 mm. Texture: Sparsely pubescent, stipulate-glandular. Color: Closest to 146A. Internode length at center of branch: Approximately 2.1 cm.

*Foliage.*—Number of leaves per main branch: Approximately 8. Fragrance: None. Form: Simple. Arrangement: Opposite. Aspect: Petiole is at an acute angle to stem and leaf blade is at an obtuse angle to stem. Shape: Ovate. Margin: Widely dentate. Apex: Acute. Base: Truncate. Venation pattern: Pinnate. Length of mature leaf: Approximately 2.0 cm. Width of mature leaf: Approximately 1.6 cm. Texture of upper and lower surfaces: Glabrous. Color of upper surface of mature foliage: 137A with venation of 143B. Color of lower surface of mature foliage: 138A with venation of 143B. Petiole length: Approximately 2.7 mm. Petiole diameter: Approximately 1.0 mm. Petiole texture: Glabrous. Petiole color: 143B.

Flowering description:

*Flowering habit.*—'Balwinwite' is freely flowering under outdoor growing conditions with substantially continuous blooming from spring through autumn and year round in greenhouse environment.

*Time to first flower.*—Approximately 10 weeks from sticking of an unrooted cutting.

*Lastingness of individual bloom.*—Approximately 3 to 4 days.

Flower description:

*Type.*—Solitary, five lobed and zygomorphic. Arrangement: Terminal racemes. Quantity per plant: Approximately 76 at 7 weeks. Fragrance: None.

*Bud rate of opening.*—Generally takes 2 to 3 days for bud to progress from first color to fully open flower.

*Bud just before opening.*—Shape: Ovate. Length: Approximately 7.6 mm. Diameter: Approximately 6.8 mm. Texture: Pubescent. Color 4D.

*Corolla.*—Shape: Obovate. Width: Approximately 2.1 cm. Length: Approximately 2.1 cm. Depth: Approximately 9.8 mm.

*Petals.*—Quantity: 5 fused at base with base of upper and lateral petals forming nectar spurs. Shape: Obovate. Aspect: Downward turning at edges. Appearance: Iridescent. Margin: Entire. Apex: Obtuse.

*Two upper petals.*—Length: Approximately 8.3 mm. Width of each: Approximately 5.1 mm. Texture: Glabrous. Color of both surfaces: 155C. Length of indentation at base: Approximately 4.2 mm. Width of indentation at base: Approximately 3.8 mm. Color of indentation at base: 2A.

*Two lateral petals.*—Length: Approximately 7.3 mm. Width of each: Approximately 8.0 mm. Texture of upper surface: Glabrous. Texture of lower surface: Glabrous with sparse stipulate glands at base where nectar spurs form. Color: 155C. Gland color: N83B.

*Single lower petal.*—Length: Approximately 1.1 cm. Width: Approximately 1.5 cm. Texture of upper surface: Glabrous with sparse sessile glands at base. Texture of lower surface: Glabrous with sparse stipulate glands at base. Color: 155C. Gland color: N83B.

*Nectar spur.*—Quantity: 2 per flower. Length: Approximatley 7.5 mm. Diameter at base: Approximately 2.7 mm. Diameter at tip: Approximately 1.1 mm. Texture: Glabrous. Color: 155C with streaks of N81B near tip.

*Pedicel.*—Strength: Moderate. Aspect: Acute angle to stem. Length: Approximately 2.0 cm. Diameter: Approximately 0.4 mm. Texture: Stipulate-glandular. Color: 143C. Gland color: N83B.

*Calyx.*—Shape: Five-pointed star. Diameter: Approximately 5.6 mm.

*Sepals.*—Quantity per flower: 5. Shape: Lanceolate. Apex: Acute. Margin: Entire. Length: Approximately 3.0 mm. Width: Approximately 1.0 mm. Texture of upper or inner surface: Glabrous. Texture of lower or outer surface: Stipulate-glandular. Color: 137C. Gland color: N83B.

*Reproductive organs.*—Androecium: Stamen quantity: 4. Filament length: Approximately 2.3 mm. Filament texture: Stipulate-glandular. Gland color: N83B. Filament color: 150D. Anther shape: Bi-lobed. Anther length: Approximately 1.0 mm. Anther color: 11B. Pollen amount: Abundant. Pollen color: 13B. Gynoecium: Pistil quantity: One per flower. Pistil length: Approximately 4.0 mm. Stigma shape: Round. Stigma length: Approximately 0.4 mm. Stigma color: Colorless, opaque. Style length: Approximately 1.6 mm. Style color: 144C. Ovary diameter: Approximately 2.0 mm. Ovary color: 144B.

Seed and fruit production: Neither seed nor fruit production has been observed.

Disease and pest resistance: Resistance to pathogens and pests common to *Diascia* has not been observed.

What is claimed is:

1. A new and distinct cultivar of *Diascia* plant named 'Balwinwite', substantially as herein shown and described.

* * * * *